United States Patent
Hombek et al.

(10) Patent No.: US 6,242,631 B1
(45) Date of Patent: Jun. 5, 2001

(54) TRIARYL PHOSPHATE ESTER COMPOSITION

(75) Inventors: Richard Hombek, Yorktown Heights; Theodore A. Marolewski, New City; Mark Buczek, Sleep Hollow, all of NY (US)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/354,694

(22) Filed: Jul. 16, 1999

Related U.S. Application Data

(63) Continuation-in-part of application No. 09/158,425, filed on Sep. 21, 1998, now abandoned.

(51) Int. Cl.$^7$ ................................................. C07F 9/12
(52) U.S. Cl. ................................................. 558/211
(58) Field of Search .............................. 558/211

(56) References Cited

U.S. PATENT DOCUMENTS

| | | | | |
|---|---|---|---|---|
| 2,071,323 | * | 2/1937 | Bass | 558/211 |
| 2,275,041 | | 3/1942 | Britton et al. | 260/461 |
| 3,780,145 | * | 12/1973 | Malec | 558/211 |
| 3,859,395 | | 1/1975 | Terhune et al. | 260/966 |
| 3,945,891 | | 3/1976 | Aai et al. | 203/77 |
| 4,087,386 | | 5/1978 | Dounchis et al. | 252/49.8 |
| 4,093,680 | | 6/1978 | Randell et al. | 260/966 |
| 4,139,487 | | 2/1979 | Garrett | 252/182 |
| 4,378,320 | * | 3/1983 | Mirviss et al. | 558/211 |
| 4,443,384 | | 4/1984 | Finley et al. | 260/982 |
| 4,492,660 | * | 1/1985 | Giolito | 558/211 |
| 5,206,404 | | 4/1993 | Gunkel et al. | 558/146 |

OTHER PUBLICATIONS

H.O. Sanders et al., "Toxicity of Seven Potential Polychlorinated Biphenyl Substitutes to Algae and Aquatic Invertebrates" Environmental Toxicology and Chemistry, vol. 4, pp. 149–154 (1985).
Chemical Abstracts, vol. 120, 191999m (1994).
Chemical Abstracts, vol. 90, 24119e (1979).

* cited by examiner

Primary Examiner—Michael G. Ambrose
(74) Attorney, Agent, or Firm—Richard P. Fennelly

(57) ABSTRACT

The invention relates to a composition of mixed alkylated triphenyl phosphate esters comprising no less than 65% to about 100%, by weight, monoalkylphenyl diphenyl phosphate, up to about 30%, by weight, dialkylphenyl phenyl phosphate, up to about 3%, by weight, trialkylphenyl phosphate, and up to about 5%, by weight, triphenyl phosphate. The alkyl moieties can be isopropyl, isobutyl tertiary-butyl, isoamyl, tertiary-amyl, isooctyl and/or isononyl.

The fluids prepared according to the previously described method show unusually low air entrainment values of less than 180 seconds, and as low as 20 seconds, and have a content of triphenyl phosphate that typically varies from about 0 to about 5.0%.

5 Claims, No Drawings

TRIARYL PHOSPHATE ESTER COMPOSITION

CROSS-REFERENCE TO RELATED APPLICATION

This is a continuation-in-part of U.S. Ser. No. 09/158,425, filed Sep. 21, 1998 now abandoned.

BACKGROUND OF THE INVENTION

The invention is a novel liquid mixed triaryl phosphate composition containing a reduced concentration of triphenyl phosphate.

Mixed synthetic triaryl phosphate esters have been prepared by alkylating phenol with alkenes, such as propylene or isobutylene, to obtain a mixture of phenol and substituted phenols. According to U.S. Pat. No. 4,093,680, this alkylate mixture can then reacted with phosphorus oxychloride ($POCl_3$) to form a mixed triaryl phosphate ester. The product mix is a statistical mixture based on the composition of the starting alkylate and always includes some fraction of triphenyl phosphate (TPP), usually from 5 to 50 percent. The product's physical properties are determined by the degree of alkylation of the phenol. A highly alkylated phenol mixture will result in a more viscous phosphate ester product than one less substituted. For example, this process results in products that are a mixture of phosphate ester isomers including: triphenyl phosphate, diphenyl alkylphenyl phosphate, phenyl di(alkylphenyl)phosphate, and tri (alkylphenyl)phosphate ("mixed alkylated phosphate esters"). It is also possible that phenol rings with 2–5 alkyl groups may be present, however, these groups are slow to react with $POCl_3$, and are present at less than 0.5% in commercial products. The final product is tailored by selecting a specific blend of phenol and alkyl phenols as starting materials.

Such phosphate esters are used as fire resistant hydraulic fluids and lubricant basestocks, lubricant anti-wear additives, and flame retardant plasticizers. A phosphate ester that is highly resistant to oxidative, thermal, and hydrolytic degradation is desirable. In addition, a phosphate ester that has low volatility will not exhibit large evaporation losses, which is advantageous for high temperature applications.

Prior phosphate esters with good oxidative stability had poor hydrolytic stability, and conversely, phosphate esters with good hydrolytic stability had reduced oxidative stability. It is desirable to produce a triaryl phosphate ester with a combination of excellent thermal, oxidative, and hydrolytic stability.

Alkylated (iso-propyl, tert-butyl, iso-octyl, isononyl) triaryl phosphate esters are useful as fire resistant hydraulic fluids, lubricants and lubricity additives. Currently used product are prepared by reaction of phosphorus oxychloride with mixture of alkylated phenols which contain significant amount of phenol. As a consequence, the resulted product contains triphenyl phosphate at concentrations well above 5%. Triphenyl phosphate is known as mild cholinesterase inhibitor and as such should be avoided in lubricants. The prior art compositions of alkylated triphenyl phosphates with low concentration of triphenyl phosphate are of high viscosity and are not useful as hydraulic fluids.

A recent example of a disclosure that is also relevant to the present invention is contained in U.S. Pat. No. 5,206,404. The products that are described in this patent that have a lower content of triphenyl phosphate were obtained by removal of triphenyl phosphate from the standard product by distillation. The resulted product is usually of high viscosity (over 85 cSt at 40° C.), and the composition contains a high concentration of multi-substituted molecules and a relatively low concentration of mono-alkylphenyl diphenyl phosphate and, as such, is not very useful in hydraulic fluid applications.

An older example of a disclosure that is also relevant to the present invention is contained in U.S. Pat. No. 2,275,041. The products that are described in this patent have a low triphenyl phosphate content and a high mono-alkylphenyl diphenyl phosphate content. However, the products described in U.S. Pat. No. 2,275,041 are too reactive to be suitable for use as hydraulic fluids where thermal stability and non-reactivity are primary performance criteria. In fact, the patentees claim their products "are useful as modifying agents for various synthetic resins, and, because of the reactivity of the allyl-type group, are particularly useful as intermediates in the preparation of a wide variety of new organic chemicals."

SUMMARY OF THE INVENTION

The invention is a novel liquid mixed triaryl phosphate ester composition with low content of triphenyl phosphate and viscosity range from about 30 to about 85 cSt @ 40° C. and a process for its manufacture. This composition shows lower air entrainment time when compared to the standard products of this type. The standard of mixed synthetic triaryl phosphate esters are prepared by phenol alkylation with alkenes to obtain mixture of phenol and alkylated phenols which is then reacted with phosphorus oxychloride. Such product contains high level of triphenyl phosphate usually much more than 5% and typical air entrainment times are in the range of 3 to 6 minutes.

Description of the Preferred Embodiments

The present invention overcomes the problems of the prior art by providing a fluid composition of mixed alkylated triphenyl phosphate esters comprising by weight:

Monoalkylphenyl diphenyl phosphate: 65–100%
Dialkylphenyl phenyl phosphate: 0–30%
Trialkylphenyl phosphate: 0–3%
Triphenyl phosphate: 0–5%

One preferred embodiment of the present invention is a composition of mixed tertiary-butylated triphenyl phosphate esters containing no less than about 80% monotert-butylphenyl phosphate, which phosphate contains from about 40% to about 60% ortho isomer, and from about 60% to about 40% para isomer, up to about 20% di-tert-butylphenyl phenyl phosphate, up to about 2% tri-tert-butylphenyl phosphate, and up to about 5% triphenyl phosphate.

The composition of the present invention is prepared by the following process: $POCl_3$ is first reacted with a high purity alkylated phenol in a quantity sufficient to exhaust at least one functionality of the $POCl_3$ reagent and the existing product is then reacted with phenol to complete the reaction. The same product can also be synthesized by reversing this reaction sequence. First, a mixture of diphenyl monochlorophosphate and phenyl dichlorophosphate is prepared in the reaction of $POCl_3$ with phenol and the reaction is completed using a high purity alkylated phenol reagent. To accelerate these reactions, a number of catalysts can be used, such as $MgCl_2$, $TiCl_4$, and others. The alkylated phenols used in the practice of the present invention are: the iso-propylphenols, the t-butylphenols, the iso-octylphenols, and the iso-nonylphenols.

The fluids prepared according to the previously described method show unusually low air entrainment values of less than 180 seconds, and as low as 20 seconds, and have a content of triphenyl phosphate that typically varies from about 0 to about 5.0%.

The importance of low air entrainment (rapid air release) for a phosphate ester hydraulic fluid is illustrated by the three minute (180 second) limit established by Siemens AG in their specification TLV 9012 02 for "Fire Resistant Fluid for Electrohydraulic Actuators". Currently, only trixylyl phosphate esters are approved for use in Siemens systems. Trixylyl phosphate esters typically have air entrainment times of thirty seconds or less. Mixed alkylated triaryl phosphate esters are not used in Siemens electrohydraulic control systems because of their typical air entrainment times of three to six minutes. The phosphate ester compositions described in the present invention are within the Siemens AG specification of three minutes and, in several cases, match the very low values of trixylyl phosphate esters.

Additionally, the fluids that are prepared according to the present invention are believed not to be cholinesterase inhibitors in contrast to current commercially available triaryl phosphate esters that have utility as hydraulic fluids.

The present invention is further illustrated by the Examples that follow.

EXAMPLE 1

Industrial grade (96 wt %) diphenylchlorophosphate was purified by distillation to a purity of 99 wt %. Then, 684 g of the purified diphenylchlorophosphate was reacted with p-tert-butylphenol (99.5%) at a temperature ranging from 120 ° C. to 170° C. for five hours. The reaction was run in the presence of 1.4 g of $MgCl_2$. The catalyst was removed by washing with water, and unreacted p-tert-butylphenol was removed under vacuum by heating the product to 100° C. Yield: 96%.

Product Composition:
  97.6 wt % of p-tert-butylphenyl diphenyl phosphate
  0.6 wt % of di-p-tert-butylphenyl phenyl phosphate
  1.8 wt % of tri-p-tert-butylphenyl phosphate Product Properties:
  Viscosity @ 40° C.: 36.9 cSt
  Foam*: 0 mL/0 seconds
  Air entrainment**: 20 seconds
  * determined using ASTM D892.
  ** determined using ASTM D3427.

EXAMPLE 2

In this Example, 549 g of industrial grade $POCl_3$ was reacted with 561 g of 99% pure o-tert-butylphenol for eighteen hours under reflux at the temperature ranging from 100° C. to 180° C. The reaction product was cooled to 100° C., and 673.2 g of phenol was added and was reacted at 120° C.–150° C. for six hours. The reaction was run in the presence of 1.1 g of $MgCl_2$ as a catalyst. The catalyst was removed by washing with water and unreacted o-tert-butylphenol was removed under vacuum by heating the product to 100° C. Yield: 94%.

Product Composition:
  86 wt % o-tert-butylphenyl diphenyl phosphate
  9.5 wt % di-o-tert-butylphenyl phenyl phosphate
  0.1 wt % tri-o-tert-butylphenyl phosphate
  4.4 wt % triphenyl phosphate Product Properties:
  Viscosity @ 40° C.: 55.5 cSt
  Foam: 0 mL/0 seconds
  Air entrainment: 40 seconds

EXAMPLE 3

In this Example, 500 g of diphenyl chlorophosphate (99% pure) and 50 g of phenyl dichlorophosphate (95% pure) were reacted with p-tert-butylphenol at 145° C. for twelve hours in the presence of 1 g of $MgCl_2$ as a catalyst. The catalyst was removed by washing with water and unreacted p-tert-butylphenol was removed under vacuum by heating the product to 100° C. Yield: 95%.

Product Composition:
  85.6 wt % p-tert-butylphenyl diphenyl phosphate
  13.7 wt % di-p-tert-butylphenyl phenyl phosphate
  0.7 wt % triphenyl phosphate Product Properties:
  Viscosity @ 40° C.: 43.8 cSt
  Foam: 0 mL/0 seconds
  Air entrainment: 90 seconds

EXAMPLE 4

In this Example, 306.6 g of reagent grade $POCl_3$ was reacted with 324 g of 99% pure p-tert-butylphenol for fourteen hours under reflux at the temperature ranging from 100 ° C. to 150° C. The reaction product was cooled to 100° C. and 361 g of phenol was added and was reacted at 145° C. for six hours. The reaction was run in the presence of 0.6 g of $MgCl_2$ as a catalyst. The catalyst was removed by washing with water and unreacted p-tert-butylphenol was removed under vacuum by heating the product to 100° C. Yield: 92%.

Product Composition:
  76.8 wt % p-tert-butylphenyl diphenyl phosphate
  19.6 wt % di-p-tert-butylphenyl phenyl phosphate
  0.4 wt % tri-p-tert-butylphenyl phosphate
  3.2 wt % triphenyl phosphate Product Properties:
  Viscosity @ 40° C.: 44.2 cSt
  Foam: 0 mL/0 seconds
  Air entrainment: 120 seconds.

EXAMPLE 5

The product from Example 1 and the product from Example 2 were mixed in a ratio of 1:1 to create a composition with air entrainment and viscosity properties meeting the Siemens AG specifications for fire resistant fluid for electrohydraulic actuators. The composition of this blended product was:
  48.8 wt % of p-tert-butylphenyl diphenyl phosphate
  0.3 wt % of di-p-tert-butylphenyl phenyl phosphate
  0.8 wt % of tri-p-tert-butylphenyl ph osphate
  43.0 wt % o-tert-butylphenyl diphenyl phosphate
  4.8 wt % di-o-tert-butylphenyl phenyl phosphate
  2.3 wt % triphenylphosphate Product Properties:
  Viscosity @ 40° C.: 46.8 cSt
  Foam: 0 mL/0 seconds
  Air entrainment: 20 seconds Since the foregoing Examples are only intended to illustrate certain embodiments of the present invention, they should not be used in a limiting sense to construe the scope of the present invention. The scope of protection sought is set forth in the Claims that follow.

We claim:

1. A composition of mixed alkylated triphenyl phosphate esters, containing at least two of said esters, which composition comprises no less than 65% to about 100%, by weight, monoalkylphenyl diphenyl phosphate, up to about 30%, by weight, dialkylphenyl phenyl phosphate, up to about 3%, by weight, trialkylphenyl phosphate, and up to about 5%, by weight, triphenyl phosphate, wherein alkyd moieties are selected from the group consisting of isopropyl, isobutyl, tertiary-butyl, isoamyl, tertiary-aryl, isooctyl and inononyl.

2. The composition of claim 1 wherein substantially all of the alkyl moieties are tertiary-butyl.

3. The composition of claim 1 wherein substantially all of the alkyl moieties are isopropyl.

4. A composition of mixed tertiary-butylated triphenyl phosphate esters comprising no less than about 80% mono-(tert-butylphenyl)diphenyl phosphate, which phosphate comprises from about 40% to about 60% ortho isomer, and from about 60% to about 40% para isomer, up to about 20% di-tert-butylphenyl phenyl phosphate, up to about 2% tri-tert-butylphenyl phosphate, and up to about 5% triphenyl phosphate.

5. The composition of claim 4 wherein substantially all of the alkyl moieties are tertiary-butyl.

* * * * *

UNITED STATES PATENT AND TRADEMARK OFFICE
CERTIFICATE OF CORRECTION

PATENT NO. : 6,242,631 B1
DATED : June 5, 2001
INVENTOR(S) : Richard Hombek et al.

Page 1 of 1

It is certified that error appears in the above-identified patent and that said Letters Patent is hereby corrected as shown below:

<u>Claim 1,</u>
Line 9, "inononyl" should read -- isononyl --

Signed and Sealed this

Twenty-ninth Day of January, 2002

Attest:

Attesting Officer

JAMES E. ROGAN
*Director of the United States Patent and Trademark Office*